United States Patent [19]

Buttaravoli

[11] Patent Number: 4,457,754

[45] Date of Patent: Jul. 3, 1984

[54] MULTI-PURPOSE SECUREMENT STRIP FOR USE ON THE BODY OF A PATIENT

[75] Inventor: Philip M. Buttaravoli, Potomac, Md.

[73] Assignee: E-Med Corporation, Cincinnati, Ohio

[21] Appl. No.: 343,855

[22] Filed: Jan. 29, 1982

[51] Int. Cl.³ ............................................ A61M 25/02
[52] U.S. Cl. ..................................... 604/180; 128/133; 128/DIG. 26
[58] Field of Search ....................... 128/133, DIG. 26; 604/174, 179, 180

[56] References Cited

U.S. PATENT DOCUMENTS

| 2,469,064 | 5/1949 | Campbell | 128/156 |
| 3,430,300 | 3/1969 | Doan | 604/180 X |
| 3,521,631 | 7/1970 | Gardner et al. | 128/156 |
| 3,826,254 | 7/1974 | Mellor | 128/133 |
| 3,834,380 | 9/1974 | Boyd | 128/133 |
| 3,918,446 | 11/1975 | Buttaravoli | 128/133 |
| 4,122,857 | 10/1978 | Haerr | 604/180 |
| 4,324,237 | 4/1982 | Buttaravoli | 604/180 |
| 4,333,468 | 6/1982 | Geist | 604/180 |

Primary Examiner—Dalton L. Truluck
Attorney, Agent, or Firm—Frost & Jacobs

[57] ABSTRACT

A multi-purpose securement strip for anchoring tubing, monitor lines and the like on a body portion of a patient. The securement strip comprises an elongated base strip of flexible material having on its underside an adhesive coating for attachment of the base strip to the patient's skin. An elongated, flexible cover strip is provided, having a first portion (including an end of the cover strip) permanently affixed to the upper surface of the base strip. The cover strip has a second portion releasably adherable to the upper surface of the base strip such that one or more tubes, monitor lines or the like can be so located as to overlie the upper surface of the base strip, transversely of the long axis of the base strip, and can be adjustably and releasably held in position on the base strip by the second portion of the flexible cover strip.

10 Claims, 8 Drawing Figures

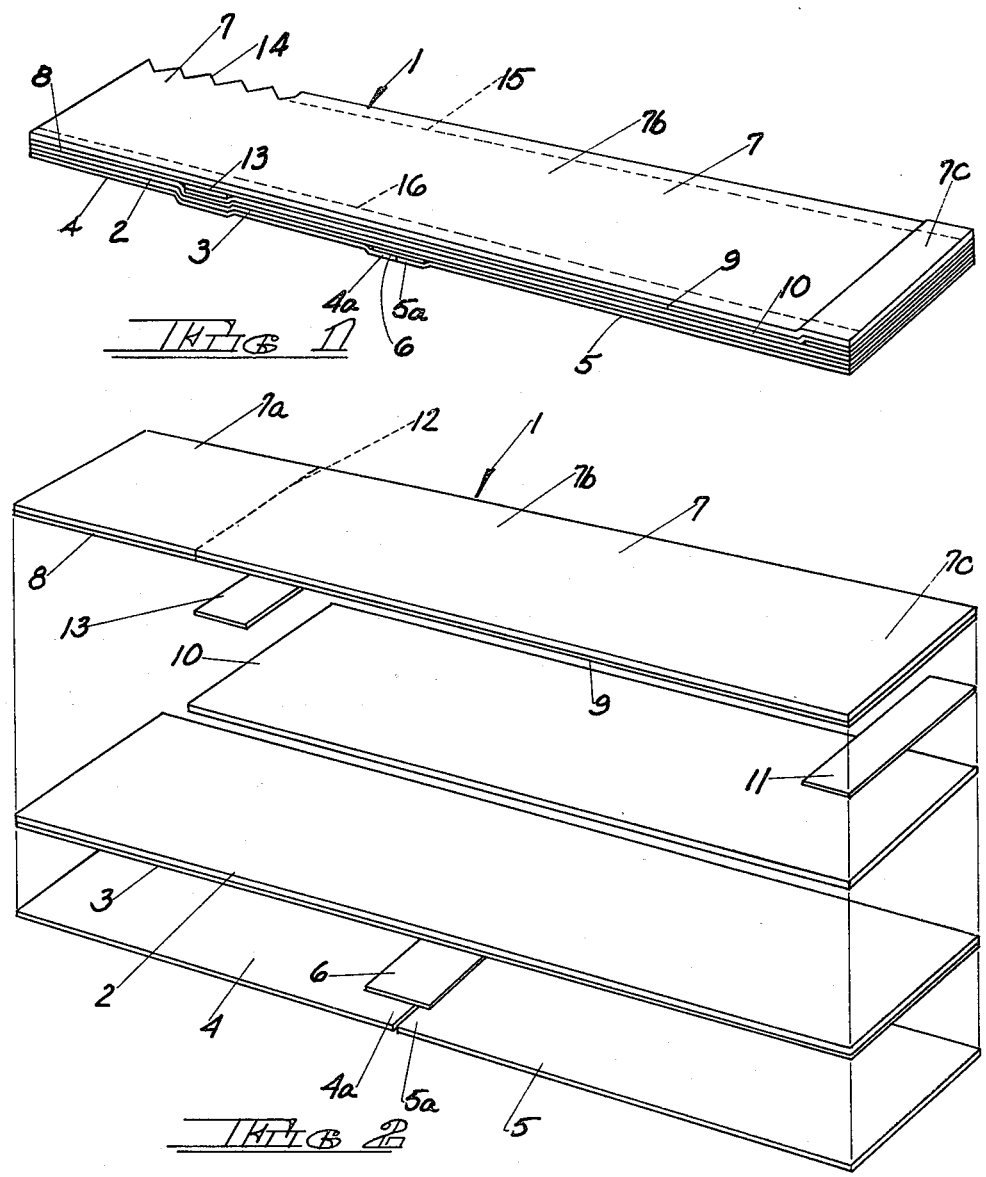

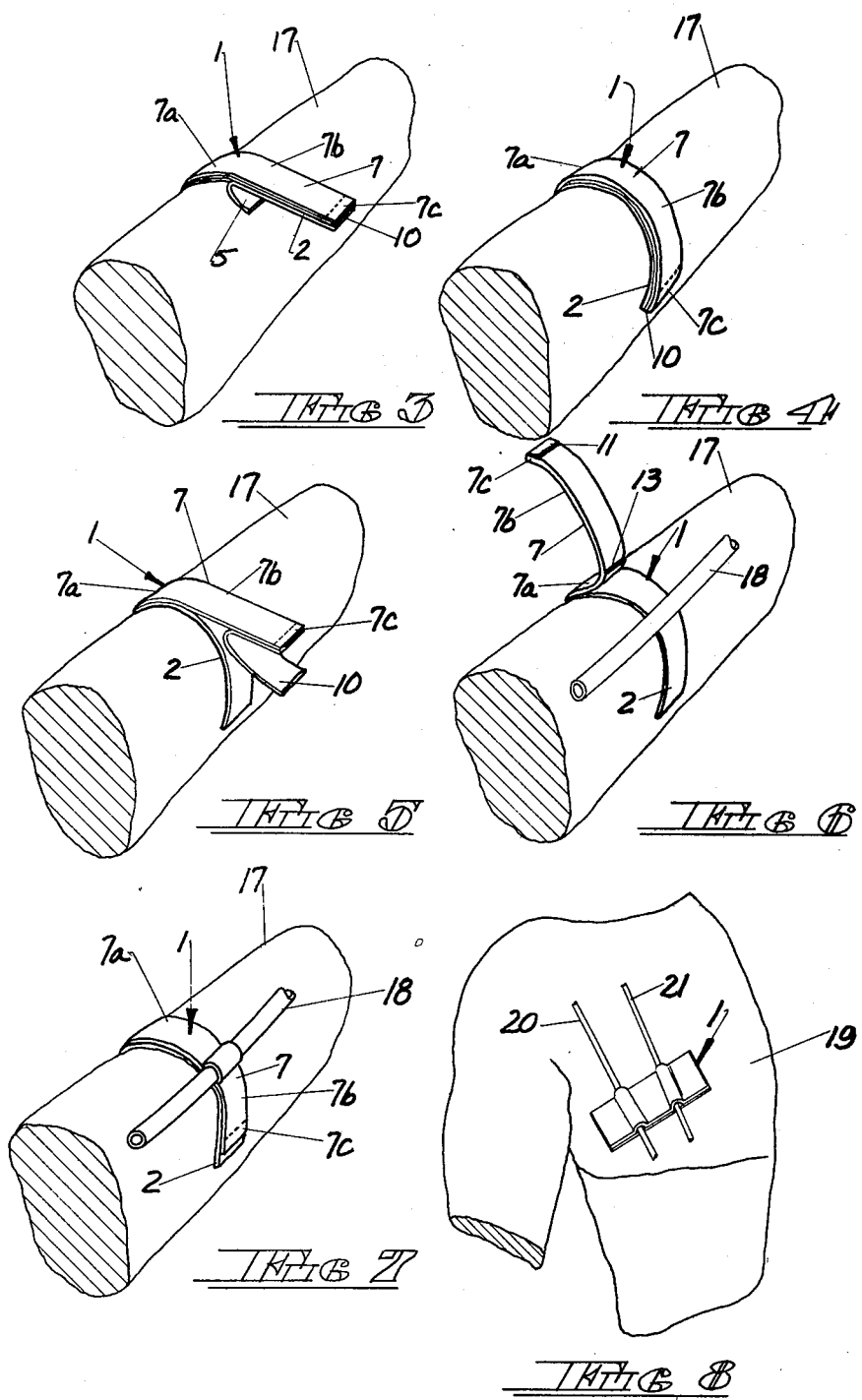

MULTI-PURPOSE SECUREMENT STRIP FOR USE ON THE BODY OF A PATIENT

REFERENCE TO RELATED APPLICATION

This application relates to a copending application Ser. No. 06/124,859, filed Feb. 26, 1980, in the name of the same inventor and entitled INTRAVENOUS CATHETER AND TUBING SECUREMENT AND DRESSING WITH A WINDOW OVER THE PUNCTURE OR WOUND SITE, now U.S. Pat. No. 4,324,237 patented on Apr. 13, 1982.

TECHNICAL FIELD

The invention relates to a multi-purpose medical securement strip and more particularly to such a securement strip by which one or more tubes, monitor lines, or other medical devices can be adjustably and removably mounted on a portion of a patient's body.

DISCLOSURE OF THE INVENTION

While the securement strip of the present invention could be used to secure any small device or tube-like structure to a particular surface, the securement device is particularly applicable to the attaching of medical tubing, monitor lines, or other small medical devices to a portion of a patient's body. Therefore, for purposes of an exemplary showing, the device will be described in its application to a multi-purpose securement for hospital tubing, monitor lines and the like.

There are numerous instances wherein it is desirable to anchor and maintain medical tubing at various positions on a patient's body. Tubing is used in many medical procedures, some examples of which include intravenous feeding, transfusions, various types of catheterization, oxygen breathing equipment and the like. In similar fashion, it is frequently desirable to anchor and maintain monitor lines at various positions on the patient's body such as lines associated with heart monitoring devices and the like.

Prior art workers have devised numerous types of devices for anchoring or attaching tube-like structures to a patient's body. For example, U.S. Pat. No. 3,146,788 teaches an adhesive coated strap adapted to engage the shank of a catheter tube. The strap, itself, is pivotally affixed by a snap to an adhesive coated second member intended to be adhered to the patient's body. However, no solid support is provided the tube, nor is it intended to be. U.S. Pat. No. 3,630,195 teaches an infusion tube holder comprising an adhesive strip intended for attachment to the patient's skin. The upper surface of the adhesive strip has a clamp means mounted thereon. The structure of this reference is exemplary of various types of clamp configurations. Such structures, however, limit what can be secured and do not provide means to prevent the tubing from sliding axially through the clamp. U.S. Pat. No. 3,677,250 teaches another prior art approach providing a tabbed anchoring tape means for surgical tubing or the like. According to this invention, one or more tabs are provided, intended to be adhered to the skin. The tab, in turn, carries a laterally extending adhesive strap intended to be wrapped about the surgical tubing. Such a structure offers no adjustability and resealability and in most embodiments the tube is capable of pivoting about the juncture between the strap and the tab.

U.S. Pat. No. 3,834,380 teaches another embodiment of the prior art clamp approach. Here, an adhesively backed tape is provided on its upper side with a clamp member. The clamp member, itself, is additionally provided with an overlying flap releasably held down by Velcro attachment means. There is no adhesive contact between the securement means and the tube being secured and the tube is not anchored against axial movement.

U.S. Pat. No. 3,826,254 teaches a catheter retaining appliance comprising an elongated strip of tape folded upon itself. The first portion or bottom layer of the structure is provided with adhesive on its lower and upper sides. The adhesive on the lower side permits this first portion to be affixed to the patient's skin. The second portion of the appliance comprises a flap having an adhesive layer only on its upper side. The catheter to be retained is mounted on the upper side of the first portion and the second portion, acting as a flap, is folded over the catheter and the first portion with their mutually adhesived surfaces in contact. As a result, the flap is not capable of being reopened, permitting adjustment of the catheter being retained. A somewhat similar structure is taught in U.S. Pat. No. 4,122,857. In this instance, a foam material pad is provided, the underside of which is coated with adhesive for attachment to the skin of a patient. A flap, substantially coextensive with the pad, is provided on the upper side of the pad. The flap may constitute a separate piece or an integral part of the pad. The underside of the flap is adhesively coated and provided with a release or backing sheet. The flap may be lifted and a tubular member located on the upper side of the pad, extending longitudinally of the pad. The backing sheet is then removed from the flap and the flap is then replaced over the tubular member to attach it to the pad. As illustrated in this reference, the pad and flap have a length dimension only about twice their width dimension thus limiting the nature of the article capable of being anchored to a patient's body by the pad. Furthermore, the flap is so arranged that the article being anchored must extend longitudinally of the pad structure. The reference does not specify that the flap is releasable and releasable to the pad for purposes of change or adjustment of the article or articles being anchored.

The above mentioned related, copending application sets forth a medical dressing having a reclosable window over the wound or puncture site and which, in one embodiment can serve as a securement device for an intravenous catheter and its tubing, and in another embodiment can serve as a dressing for a wound. In all embodiments, the dressing device comprises a base strip to which, on its upper surface, is secured a flap-like strip. A portion of the flap-like strip is releasable and resealable with respect to the upper surface of the base strip. In all embodiments of the application the base strip is provided with an opening or window in the area of the wound or puncture site and a gauze pad is located over the wound or puncture site. The gauze pad is affixed either to the base strip or the flap-like strip.

The present invention is based upon the discovery that a multi-purpose securement strip of remarkable simplicity, versatility and ease of use can be achieved by providing an elongated base strip having an adhesive coating on its underside for attachment to a portion of the patient's body. A cover strip, substantially coextensive with the base strip, has a first portion (including one end thereof) permanently affixed to the upper surface of the base strip, the remainder of the cover strip being provided with an adhesive which is releasably sealable and resealable to the remainder of the upper surface of the base strip. As a result, one or more elongated articles, such as hospital tubes, monitor lines, and the like, can be located on and transversely of that portion of the base strip normally covered by the second portion of the cover strip and can be adhered thereto by the second portion of the cover strip. The releasable adhesive on second portion of the cover strip will also adhere to the articles being affixed to the base strip thus precluding rotation or axial shifting thereof. The securement strip of the present invention enables easy placement, adjustment and removal of the tubes, monitor lines or other devices being held thereby.

DISCLOSURE OF THE INVENTION

According to the invention there is provided a multi-purpose securement strip for fastening tubing, monitor lines and the like on a body portion of a patient. The securement strip comprises a base strip of flexible material. The base strip has on its underside an adhesive coating whereby it can be attached to the patient's skin. The adhesive coating on the underside of the base strip is provided with at least one disposable protective liner member.

A flexible cover strip is provided which is substantially coextensive with the base strip. The flexible cover strip has a first portion (including one end of the flexible cover strip) which is permanently affixed to the upper surface of the base strip. The cover strip has a second portion, the underside of which is coated with a releasable and resealable adhesive, by which the second portion of the cover flap can be releasably sealed to the corresponding portion of the upper surface of the base strip. A disposable protective liner is provided for the adhesive coating on the underside of the second portion of the cover strip.

To complete the structure, the free end of the second portion of the cover strip is provided with means to prevent its adherence either to the protective liner or to the upper surface of the base strip. Thus, a narrow transverse portion of the free end of the second portion of the cover strip constitutes a pull tab enabling easy removal of the protective liner for the second portion of the cover strip, and also enabling lifting of the cover strip from the base strip when adhered thereto in use.

The multi-purpose securement strip is affixed to the patient by removing the one or more protective liners from the adhesive layer on the base strip and pressing the base strip onto the body of the patient at the desired position. The second portion of the cover strip is then lifted and one or more hospital tubes, monitor lines or other appropriate elements are placed upon the upper side of the base strip, extending transversely thereof. With the elements to be anchored properly located in place, the protective liner is removed from the second portion of the cover strip and the second portion of the cover strip is adhered to the upper surface of the base strip and to the elements to be anchored. When it is desired to rearrange or reposition these elements or to substitute different elements, it is only necessary to lift the second portion of the cover strip, detaching it from the upper surface of the base strip and the elements. The necessary changes or adjustments are made and then the second portion of the cover strip is resealed to the base strip and the elements to be anchored.

BRIEF DESCRIPTION OF THE DRAWINGS

FIG. 1 is a perspective view of the multi-purpose securement strip of the present invention.

FIG. 2 is an exploded perspective view of the securement strip of FIG. 1.

FIGS. 3 through 7 are fragmentary perspective views illustrating the placement and use of the securement strip on a body portion of a patient.

FIG. 8 is a fragmentary perspective view illustrating the placement of the securement strip on another body portion of a patient and the use of the strip to anchor more than one elongated element.

DETAILED DESCRIPTION OF THE INVENTION

Reference is first made to FIG. 1 and 2 wherein like parts have been given like index numerals. Throughout the drawings the various plies or layers of cloth tape and liner material, and particularly the adhesive layers, have been exaggerated in thickness for purposes of clarity. FIG. 1 illustrates the embodiment ready for use. FIG. 2 is an exploded view of the embodiment of FIG. 1.

The multi-purpose securement strip is generally indicated at 1. It comprises a base strip 2 which may be made of any flexible material appropriate for use in a medical environment. Preferably, the base strip 2 is made of a medical grade cloth, foam or plastic tape having on its underside a coating of adhesive 3 suitable for adhering the base strip 2 to the patient's skin. Both the tape and the adhesive may be selected from those, well known in the art for their hypoallergenic and adhesive qualities.

While the dimensions of the base strip 2 do not constitute a limitation on the present invention, it is desirable that the base strip 2 have a length dimension considerably greater than its width. In the exemplary application being described, i.e. a multi-purpose securement strip for hospital tubes, monitor lines and the like, excellent results have been achieved with a base strip 2 having a length to width ratio of about 6:1, the base strip being about 6 inches long and about 1 inch wide.

In the preferred embodiment, a pair of conventional, removable, disposable liners 4 and 5 are provided to protect the adhesive layer 3 of base strip 2. Liners 4 and 5 each extend approximately one-half the length of base strip 2 with their adjacent ends 4a and 5a meeting at about the longitudinal center of base strip 2. A narrow liner element 6 is permanently affixed to the adhesive layer 3 of base strip 2. The narrow liner element 6 extends transversely of base strip 2 at about its longitudinal center. In the fully assembled multi-purpose securement strip, it will be noted that the adjacent ends 4a and 5a of liners 4 and 5 overlie liner element 6. This being the case, the adjacent ends 4a and 5a of liners 4 and 5 are not adhered to adhesive layer 3 and therefore can serve as pull tabs for ease in removal of the liners for application of the securement strip to the skin of a patient.

The use of adjacent liner ends 4a and 5a as pull tabs could be accomplished in other ways. For example, a narrow band of non-stick coating could be applied to the underside of base strip 3 in place of liner element 6. Alternatively, the adhesive coating 3 could be eliminated on a narrow transverse portion of the underside of base strip 3 at about the longitudinal center thereof.

It would also be within the scope of the invention to provide a single conventional, disposable, removable liner coextensive with base strip 2. With such a liner (not shown) it would be preferable to have one or the other of its ends serve as a pull tab. This can be done in any of the ways just described.

A cover strip is shown at 7. The cover strip 7 may be made of the same material as base strip 2. It is preferred that cover strip 7 be of the same dimensions and coextensive with base strip 2, as shown in FIGS. 1 and 2. However, the cover strip need not be of the same dimensions or shape as base strip 2, so long as it is of sufficient size to perform its functions described hereinafter.

Cover strip 7 has a first portion 7a which preferably is permanently affixed to the upper surface of base strip 2. This can be accomplished by a nonreleasable adhesive layer 8 on the underside of cover strip portion 7a. Alternatively, the nonreleasable adhesive layer 8 could be located on the corresponding portion of the upper surface of base strip 2. The permanent joinder of cover strip portion 7a to base strip 2 could even be accomplished by mechanical means such as sewing or the like.

The remainder of cover strip 7 constitutes a second or flap portion 7b and is provided on its underside with a layer 9 of releasable and resealable adhesive. Such adhesives are well known in the art. The adhesive layer 9 is protected by a removable liner 10, similar to liners 4 and 5. In FIGS. 1 and 2, the adhesive layers 3, 8 and 9 are illustrated as separate visible layers, for purposes of description and explanation. It will be understood that these are adhesive coatings on the undersides of base strip 2 and cover strip 7 and would not, in reality, appear as separate layers having a noticeable thickness dimension.

It is preferable to have the endmost part 7c of the free end of second cover strip portion 7b constitute a tab which is not adhered to liner 10. In this way, the endmost part 7c of cover strip 7 can constitute a tab which can be readily lifted from liner 10 so that liner 10, in turn, can be easily removed from the underside of second cover strip portion 7b. This can be accomplished in substantially the same ways described with respect to liner end portions 4a and 5a, above. Thus, an additional narrow liner element 11 can be permanently adhered to the endmost portion 7c of cover strip 7. Alternatively, the adhesive layer 9 may stop short of the endmost portion 7c, or the underside of the endmost portion 7c may be provided with a non-adhesive coating. In any event, the conversion of endmost cover strip portion 7c into a pull tab or lift tab not only facilitates removal of liner 10 from cover strip portion 7b, but also facilitates lifting of cover strip portion 7b from base strip 2, when adhered thereto in use.

It will be evident from FIG. 2 that the juncture of cover strip portion 7a having adhesive layer 8 on its underside and cover strip portion 7b having adhesive layer 9 on its underside constitutes a hinge line (shown in FIG. 2 by broken line 12). It would be possible to fold liner 10 in such a way as to have a portion (not shown) folded back upon itself for about ⅛ inch or so, adjacent hinge line 12, to serve as a tab for liner 10. Preferably, however, yet another narrow transversely extending liner element 13 is provided, similar to liner element 11. The liner element 13 is permanently affixed to the underside of cover strip portion 7b adjacent hinge line 12. The narrow, transversely extending liner element 13 not only would facilitate removal of liner 10 from its end adjacent hinge line 12, but also would assure that hinge line 12 is well defined. When liner elements 11 and 13 are both present, liner 10 can easily be grasped at either of its ends for purposes of removal from cover strip 7. As in the case of liner element 11, it would be within the scope of the invention to simply cause adhesive layer 9 to stop short of hinge line 12 or apply a narrow transverse coating of non-stick material in lieu of liner element 13.

It is desirable that the longitudinal edges of base strip 2 and cover strip 7 be serrated when the strips are made of cloth tape, to prevent unraveling. Where the structure of FIGS. 1 and 2 is assembled as a continuous structure, cut transversely to form the individual securement strip, these cuts could be made with a serrated cutting means with the result that the longitudinal corresponding edges of liners 4 and 5, base strip 2, liner 10 and cover strip 7 would all be serrated. Such serrated edges are shown in part at 14 in FIG. 1 with the remainder of the serrated edges diagrammatically indicated by broken lines 15 and 16.

Various modifications may be made in the securement strip of FIGS. 1 through 2, which modifications fall within the scope of the present invention. For example, one or both of the adhesive layers 8 and 9 on the underside of cover strip 7 could be applied to the upper surface of base strip 2. In such an instance, the narrow, transverse liner elements 11 and 13, as well as liner 10, would be affixed to the upper surface of base strip 2. The adhesive coating 8 or other means affixing cover strip portion 7a to base strip 2 can be such as to make this attachment permanent, as indicated above. It would be within the scope of the invention, however, to provide an adhesive layer 8 which would make this attachment more difficultly releasable than the portion 7b, or as releasable and resealable as the portion 7b. For most uses, however, it is preferable that this attachment be permanent or at least more difficultly releasable.

FIGS. 3 through 7 sequentially illustrate an exemplary application and use of the securement strip of FIGS. 1 and 2. Again, like parts have been given like index numerals. Reference is first made to FIG. 3 wherein a patient's arm is fragmentarily shown at 17. To apply the securement strip, the liner 4 is first removed and the corresponding portion of base strip 2 is adhered to the patient's arm 17. Thereafter, the liner 5 may be removed. The liner 5 is shown in the process of being removed in FIG. 3. With liner 5 removed, the entire base strip may be adhered to the patient's arm, as shown in FIG. 4. Thereafter, the second or flap portion 7b of cover strip 7 is lifted and pivoted about its hinge line 12 (see FIG. 2). At this stage liner 10 can be removed from the underside of cover strip flap portion 7b. By virtue of the narrow, transversely extending liner elements 11 and 13, the liner 10 can be readily engaged at either of its ends and stripped from the underside of cover strip flap portion 7b. In FIG. 5, liner 10 is shown in the process of being removed from its end nearest hinge line 12 (see FIG. 2).

With liner 10 removed, the cover strip flap portion 7b can be lifted out of the way and the device to be anchored to the patient's body by the securement strip 1 can be so positioned as to extend across base strip 2, as shown in FIG. 6.

The nature of the device to be anchored does not constitute a limitation on the present invention except that its size must be such that it can be engaged by cover strip flap portion 7b with enough of the free end of the flap portion remaining to enable it to be securely adhered to the upper surface of base strip 2. For purposes of an exemplary showing, the member to be anchored to the arm is illustrated in FIG. 6 as being a section of hospital tubing.

Once the tubing 18 is properly positioned, the flap portion 7b of securement strip 1 is laid down along the upper surface of base strip 2 and about the tube 18. This is shown in FIG. 7. It will be evident from FIG. 7 that the tubing 18 is securely held to the patient's arm. The engagement of tube 18 by cover strip flap portion 7b will assure that the tube cannot rotate or shift axially. Nevertheless, since the adhesive coating 9 on the underside of cover strip flap portion 7b is releasable and resealable, by engagement of the free end or lift tab part 7c of cover strip flap portion 7b, the flap portion can readily be lifted from base strip 2 and tube 18 enabling the tube to be repositioned, removed or replaced by some other device. It will further be evident from FIGS. 6 and 7 that more than one tube could be simultaneously anchored by securement strip 1.

Simply for purposes of another exemplary showing, FIG. 8 fragmentarily illustrates a portion 19 of a patient's chest. A securement strip 1 of the present invention is mounted on the patient's chest and is used to anchor a pair of monitor lines shown at 20 and 21.

From the above description it will be evident that the securement strip of the present invention is fast and easy to use. The resealability of cover strip flap portion 7b enables the element or elements being anchored to be readily adjusted, changed or removed. Since the securement strip does not extend completely about the patient's body portion to which it is attached, it will have no tourniquet effect. The securement strip will prevent lateral, axial or rotational movement of the element being anchored. The provision of the various narrow, transversely extending liner elements greatly facilitate manipulation of the securement strip and its protective, disposable liners.

Modifications may be made in the invention without departing from the spirit of it.

What is claimed is:

1. An elongated multi-purpose securement strip for anchoring at least one medical device on a patient, said securement strip comprising an elongated, flat base strip having upper and lower surfaces, an adhesive coating on said lower surface of said base strip to attach said base strip to said surface, an elongated flat cover strip having upper and lower surfaces and being of the same dimensions as and co-extensive with said base strip, a first portion of said cover strip including an end thereof being affixed to a corresponding portion of said upper surface of said base strip, a second portion of said cover strip being releasably and resealably affixable to said base strip upper surface by releasable and resealable adhesive and being shiftable between an open position and a closed position adhered to said upper surface of said base strip, a narrow liner element permanently affixed to said lower surface of said second portion of said cover strip and extending transversely at the free end thereof, converting said free end of said second portion of said cover strip to a pull tab for shifting said second portion of said cover strip from said closed to said open position, said base strip and cover strip being made of medical grade cloth, foam or plastic tape, two removable and disposable protective liners for said adhesive coating on said lower surface of said base strip, said liners having opposed end edges meeting at about the longitudinal center of said base strip and extending transversely thereof, a narrow liner element permanently affixed to said lower surface of said base strip and extending transversely thereof at the longitudinal center thereof, said narrow liner element underlying said opposed end edges of said protective liners enabling said opposed end edges to serve as pull tabs for removal of said two protective liners.

2. The securement strip claimed in claim 1 wherein said first portion of said cover strip is equivalent in length up to about one third the length of said base strip.

3. The securement strip claimed in claim 1 including a removable and disposable protective liner for said releasable and resealable adhesive.

4. The structure claimed in claim 1 wherein said releasable and resealable adhesive is coated on said lower surfaces of said second portion of said cover strip and including a removable and disposable protective liner for said resealable and releasable adhesive coating.

5. The securement strip claimed in claim 1 wherein said device includes medical tubing, monitor lines and I.V. filters.

6. The securement strip claimed in claim 1 wherein the longitudinal edges of said securement strip are serrated.

7. The securement strip claimed in claim 1 including a removable and disposable protective liner for said releasable and resealable adhesive.

8. The structure claimed in claim 7 wherein said releasable and resealable adhesive is coated on said lower surface of said second portion of said cover strip and said removable and disposable protective liner for said resealable and releasable adhesive coating is mounted on said lower surface of said cover strip second portion.

9. The securement strip claimed in claim 8 wherein the longitudinal edges of said securement strip are serrated.

10. The securement strip claimed in claim 1 including a narrow liner element permanently affixed to said lower surface of said second portion of said cover strip and extending transversely thereof adjacent the juncture of said first and second portions thereof, said narrow liner element underlying an end of said protective liner for said releasable and resealable adhesive coating for easy removal of said protective liner.

* * * * *